United States Patent [19]

Charm

[11] Patent Number: 4,760,018
[45] Date of Patent: Jul. 26, 1988

[54] RAPID METHOD FOR THE DETECTION OF BETA-LACTAMASE IN BODY FLUIDS

[75] Inventor: Stanley E. Charm, Newton, Mass.

[73] Assignee: Penicillin Assays, Inc., Malden, Mass.

[21] Appl. No.: 745,431

[22] Filed: Jun. 17, 1985

[51] Int. Cl.$^4$ .................... G01N 33/566; C12Q 1/34
[52] U.S. Cl. ............................ 435/7; 435/18
[58] Field of Search ............... 435/18, 34, 35, 832, 435/7

[56] References Cited

U.S. PATENT DOCUMENTS

| | | | |
|---|---|---|---|
| 4,238,521 | 12/1980 | Charm | 426/580 |
| 4,239,745 | 12/1980 | Charm | 436/501 |
| 4,239,852 | 12/1980 | Charm | 435/32 |
| 4,353,824 | 10/1982 | Schindler | 435/18 X |
| 4,390,622 | 6/1983 | Cartwright | 435/18 |
| 4,448,880 | 5/1984 | Schindler et al. | 435/18 |

OTHER PUBLICATIONS

Yolken et al., J. Pediatrics, 97(5): 715–719 (1980).
Scudamore et al., Can. J. Microb., 22(1): 76–82 (1976).

*Primary Examiner*—Esther M. Kepplinger
*Attorney, Agent, or Firm*—Richard P. Crowley

[57] ABSTRACT

A rapid method for the detection of beta-lactamase in body fluids which method comprises contacting a sample of a body fluid with charcoal, removing the charcoal and recovering an essentially charcoal free supernatant, adding a labeled beta-lactam compound such as $C^{14}$ penicillin to the supernatant for a defined period of time, adding a antibiotic sensitive microorganism, incubating and thereafter removing the microorganism cells from the incubation broth, measuring the amount of $C^{14}$ bound-labeled penicillin and comparing the measured amount with a controlled sample or standard data or graph to determine the amount of any beta-lactamase in the body fluid sample.

8 Claims, No Drawings

RAPID METHOD FOR THE DETECTION OF BETA-LACTAMASE IN BODY FLUIDS

BACKGROUND OF THE INVENTION

Enzymes are often found in infectious bacteria typically having a molecular weight of under 50,000, and which enzymes antagonize the antibacterial action of antibiotic drugs. For example, penicillinase, a beta-lactamase, is often found in infectious bacteria and which causes the enymatic breakdown of beta-lactam-type drugs used to treat that bacteria, such as penicillin. Thus, before an infection for a microorganism or a bacteria can be treated, it is typically advantageous to determine from a sample of a body fluid whether or not the microorganism generates a beta-lactamase, so as to determine whether the infection from the microorganism or bacteria may be treated with a beta-lactam-type drug. If a microorganism contains penicillinase, then the infection cannot be treated with a penicillin or a penicillin-type beta-lactam antibiotic drug that can be destroyed by the beta-lactamase.

Presently available methods for detecting beta-lactamase in microorganisms are not wholly satisfactory and are not rapid techniques. One method comprises culturing the microorganism and determining its resistance to the beta-lactam drug which method takes from 24 to 48 hours. Another method involves determining beta-lactamase by employing column chromatography. This test method takes about 2 hours. The need for the rapid diagnosis of infections caused by beta-lactamase in bacteria and the difficulties caused by the presence of beta-lactamase in bacteria is set forth for example in an article of *The Journal of Pediatrics* in November 1980 by R. H. Yolken et al. In this publication there is proposed a rapid diagnosis of infections caused by beta-lactamase producing bacteria by means of an enzyme radioisotopic assay technique. In the proposed test both penicillin (a beta-lactam drug), and beta-lactamase give positive tests in the proposed test.

The receptor for beta-lactam drugs is on a microbial cell which is a second reagent in the assay. If a beta-lactamase is present in the fluid to be tested, it destroys the $C^{14}$ penicillin used in the assay by degrading the beta-lactam ring. This prevents the binding of the $C^{14}$ penicillin reagent to the receptor site on the microorganism reagent. Unlabeled penicillin in the sample also prevents $C^{14}$ penicillin from binding to the receptor sites by competition for these sites. Thus, the presence of both beta-lactamase and a beta-lactam drug in the test sample results in low $C^{14}$ attachment to the microbial receptor making for a positive test result. If beta-lactamase or penicillinase is present, this test signals that a beta-lactam drug is not useful for treatment when the beta-lactamase is present.

Thus, it is desirable to provide a method for the detection of beta-lactamase, (such as penicillinase) in infectious causing microorganisms and bacterias so as to provide an easy, simple, and rapid test to distinguish between penicillinase and penicillin.

SUMMARY OF THE INVENTION

The present invention relates to a method for detecting beta-lactamase, and in particular, the method concerns a rapid and effective method for the detection of penicillinase in body fluids uncontaminated by the presence of penicillin.

The invention comprises a rapid method for the detection of beta-lactamase, (such as penicillinase) in body fluids, which method comprises exposing a sample, for example, of a body fluid to an absorbent, such as charcoal to provide for the absorption of any beta-lactam in the body fluid, (such as a penicillin) to the absorbent and thereafter removing the charcoal, for example, by filtration or centrifuge and recovering an essentially charcoal-free, beta-lactam-free supernatant fluid. A labeled beta-lactam drug, such as an isotope e.g. $C^{14}$ labeled beta-lactam compound such as $C^{14}$ penicillin is then added in a predetermined amount to the supernatant fluid, (such as a penicillin-like benzyl or other beta-lactam) which would be enzymatically or otherwise biodegraded in the presence of a beta-lactamase, (such as penicillinase). Incubation is carried out in the presence of an antibiotic-sensitive microorganism under conditions which allow the beta-lactam compounds to compete for and to attach to receptor sites in or on the microorganism. The microorganisms with the attached label or unlabeled beta-lactam are then removed from the incubation broth and a measure of the amount of bound labeled beta-lactam is then made and compared with a control sample to determine the presence of and the quantitative amount of any beta-lactamase present in the body fluid sample.

In the method for detection of a beta-lactamase in body fluids, the step of employing a labeled beta-lactam compound, together with a microorganism and the use of a penicillin-sensitive microorganism such as *Bacillus stearothermophilus* is disclosed in U.S. Pat. No. 4,239,852, issued Dec. 16, 1980 and U.S. Pat. No. 4,239,745, issued Dec. 16, 1980, both of which are hereby incorporated by reference in their entirety. These patents describe an antibiotic detection method for the detection of very small quantities of antibiotics, such as penicillin in milk. The process comprises the step of incubating the milk sample with a sensitive microorganism to said antibiotic that is to be detected, so as to allow the antibiotic molecules (if present) in the milk to bind to the receptor site of the microorganism, then incubating the mixture with an enzyme tag substance capable of binding with said receptor sites, separating the cells from the liquid and then determining the amount of the enzyme tag substance associated with the separated cells with a standard. This method is known as the CHARM TEST (a registered trademark of Penicillin Assays Inc. of Malden, Mass.).

Generally, the enzyme tag substance includes a beta-lactam, while the microorganism is a beta-lactam sensitive microorganism, such as and preferably *Bacillus stearothermophilus*. However, any microorganism may be used that binds to a beta-lactam drug, such as by way of example, but not limitation *Staphylococcus aureus, sorcina lutea, Bacillus substilis,* etc. The penicillin or antibiotic used preferably is a carbon 14 tag substance typically selected from a group of 6 amino penicillin acid and benzyl-penicillin or other $C^{14}$ tag penicillin compounds. Typical labeled penicillin would comprise, but not be limited to enzyme, isotope, or fluorescent labeled penicillin. For example, a peroxidase labeled penicillin, an alkaline phosphatase labeled penicillin, a fluorescent labeled penicillin signal etc. The method cannot be directly applied to the radioassay determination of the beta-lactamase in the body fluid, since in such a test method both beta-lactamase and beta-lactam result in a low count; therefore, it is necessary to remove any beta-lactam compounds or antibiotic beta-lactam drugs present in the body fluid in order to show that the beat-lactam antibiotics are not interfering with the test or that their presence is being confused with a beta-lactamase, such as penicillinase.

Further, U.S. Pat. No. 4,238,521, issued Dec. 9, 1980, hereby incorporated by reference in its entirety, is directed to a process for the removal of antibiotic compounds from milk, such as the removal of penicillin from low volume penicillin-contaminated milk. In the process the contaminated milk is exposed to an activated charcoal and recovered as an essentially penicillin-free milk product. The charcoal is subsequently removed from the milk product or the milk passes through a fixed charcoal bed. The process provides a method of recycling penicillin contaminated liquid milk through the use of activated charcoal particulate matter or a charcoal bed. The process provides for upgrading penicillin contaminated milk and milk products.

The present invention concerns the removal of penicillin or other beta-lactam antibiotics by absorption (by such substances as activated charcoal) from the body fluid sample and the subsequent testing of the penicillin-free body fluid sample by the CHARM TEST method which permits a rapid, simple method for the detection of beta-lactamase in body fluids and permits the rapid determination as to whether a beta-lactam-type antibiotic drug be employed in treating an infection.

The method for the detection of beta-lactamase may be employed in a wide variety of body fluids to include and not be limited to: cerebrospinal fluid; pleural fluid; peritoneal fluid; urine and blood and may be employed in the detection and treatment of humans and animals. The absorbent material employed for the absorption of the antibiotic may be any material which absorbs (which term also includes adsorbs) the interfering antibiotics and removes the antibiotic from the body fluid, but more typically comprises a charcoal and more particularly particulated activated charcoal which typically is merely added to the body fluid sample and admixed therewith, such as by shaking for a selected period of time from one to five minutes or more and then a supernatant recovered either by a centrifuge or filtration to provide an essentially charcoal-free body fluid sample. The contact with the absorbent should be under such conditions and for such a period of time, so as to permit the absorption of essentially all of the antibiotic in the body fluid sample onto the charcoal, so that the remaining antibiotic will not be confused with a beta-lactamase in the subsequent testing.

A labeled signal-type beta-lactam drug is added to the essentially antibiotic-free supernatant, such as an isotope labeled penicillin, but particularly a carbon 14 tag labeled drug, for example, of 6 amino penicillinoic acid or benzyl-penicillin. The tagged penicillin or beta-lactam drug is then incubated for various periods of time, for example, from about 5 to 30 minutes or more if desired with the supernatant. If there is no beta-lactamase or penicillinase present in the body fluid then no enzymatic breakdown of the tagged penicillin occurs and all of the tagged $C^{14}$ penicillin will subsequently bind to the cells of the antibiotic sensitive microorganism previously added to the body sample. If penicillinase is present, then a portion of the tagged penicillin will be enzymatically degraded and only the remaining intact tagged penicillin will react with the microorganism.

In the CHARM TEST if penicillin is present other than carbon 14 penicillin, it competes with the labeled penicillin for sites on the microorganism with the net result that it is unable to distinguish between penicillin or penicillinase. Thus, the present method requires the removal of the beta-lactam (or penicillin) in the sample prior to the adding of the tagged antibiotic compound.

The time of incubation may vary, the longer the incubation, the lower level of the beta-lactamase that may be detected by the method. A antibiotic sensitive or reactive microorganism, such as the *Bacillus stearothermophilus* is then added and incubated (for example at 37° C.) for 5 to 30 minutes, which permits the microorganism cells to react with any tagged penicillin in the body fluid sample. The *Bacillus stearothermophilus* microorganism tends to work rapidly at high temperatures in a speedy manner, so that incubation of the cells and the body serum can be for about 3 minutes at 90° C. For example, at the end of about 3 minutes incubation at 90° C., fluid in a test tube would be about 60° to 65° C. This incubation allows any carbon 14 penicillin which remains to bind to the microorganism cells. The microbial cells containing the tagged penicillin are separated from the fluid by a centrifuge and then the amount of $C^{14}$ antibiotic is then determined through the use of a counter and compared with a control or a standard data or curve to determine the presence and amount of the beta-lactamase in the sample. The higher the count of this counter, the more tagged $C^{14}$ penicillin there is bound to the microorganism. The lower the count, the less $C^{14}$ the penicillin is bound indicating that increased amounts of penicillinase are present in the body fluid.

The method of the invention will be described in connection with particularly illustrated examples; however, it is recognized that various changes, additions, and improvements may be made all falling within the spirit and scope of the inventive method.

DESCRIPTION OF THE EMBODIMENTS

Exhibit

A method for the detection of penicillinase in bovine serum was carried out as follows: 30 ul penicillinase (10 L.U./0.10 ul) was added to a test sample of bovine serum with 0.008 u/ml penicillin. 0.3 ml of fine activated charcoal particulate suspension (coated with dextran) was added to 5 ml serum in a test tube. The test tube was shaken for 1 minute, held for 2 more minutes and then centrifuged 3 minutes. The supernatant was poured from the first test tube into a second tube to remove the charcoal from the supernatant. A $C^{14}$ penicillin ($C^{14}$ benzyl-penicillin) was added to the serum and allowed to incubate at room temperature for 5 minutes. This time period gives the beta-lactamase (or penicillinase) which might be present in the serum time to break down the penicillin $C^{14}$. A penicillin sensitive microorganism (*B. stearothermophilus*) was added to the blood serum and the test is carried on through the usual procedure for the CHARM TEST. The test method takes about 25 minutes to complete. A count on the test blood serum that is at least 20% (representing about 3 standard deviations, a significant difference from zero) lower than a zero control indicates the presence of beta-lactamase in the sample.

| EXPERIMENTAL RESULTS | | |
|---|---|---|
| | Initial Count | After (8 min) |
| (a) 0.008 u/ml penicillin serum without beta-lactamase after | 455 | 430 |

-continued

| EXPERIMENTAL RESULTS | | |
| --- | --- | --- |
| | Initial Count | After (8 min) |
| charcoal treatment | | |
| (b) 0.008 u/ml penicillin serum with penicillinase added but treated with charcoal to remove penicillin | 139 | 106 |
| (c) Zero control (no penicillin or penicillinase) | 447 | 435 |
| (d) 0.008 u/ml penicillin milk treated with charcoal | 425 | 412 |
| (e) 0.008 u/ml penicillin milk (not treated with charcoal) and penicillinase | 262 | 271 |
| (f) Zero control blood serum (i.e. no penicillin no penicillinase) | 492 | 476 |
| (g) Blood serum with 0.008 u/ml penicillin no charcoal treatment | 310 | 378 |

The test method and experimental results indicated that the charcoal removes the interfering penicillin from the sample and provided for low counts in charcoal tested samples due solely to the presence of penicillinase without interference from or confusion with penicillin in the sample.

I claim:

1. A method for the detection of beta-lactamase in a body fluid sample which method comprises:
   (a) contacting a body fluid sample selected from the group consisting of cerebrospinal fluid, pleural fluid, peritoneal fluid, urine and blood to be detected for beta-lactamase with a solid absorbent for beta-lactams which would be biodegraded in the presence of a beta-lactamase to absorb any interfering beta-lactams and recovering an essentially absorbent-free, beta-lactam-free supernatant;
   (b) incubating the said supernatant with cells of a beta-lactam sensitive microorganism and a signal labeled beta-lactam capable of binding to the microorganism cells under such conditions to permit any beta-lactamase present to enzymatically degrade the labeled beta-lactam and permit the remaining intact beta-lactam to bind to the cells of the microorganisms;
   (c) removing the microorganism cells from the microorganism-supernatant mixture;
   (d) determining the amount of bound labeled beta-lactam with the removed microorganism cells; and
   (e) comparing the amount of bound labeled beta-lactam with a control sample to obtain a determination of the amount of beta-lactamase present in the sample.

2. The method of claim 1 wherein the solid absorbent comprises activated particulate charcoal.

3. The method of claim 1 wherein the beta-lactam comprises penicillin and the beta-lactamase comprises penicillinase.

4. The method of claim 1 wherein the beta-lactam sensitive microorganism comprises *Bacillus stearothermophilus*.

5. The method of claim 1 wherein the labeled beta-lactam comprises an enzyme, fluorescent or isotope labeled penicillin.

6. The method of claim 5 wherein the isotope labeled penicillin comprises $C^{14}$ penicillin.

7. The method of claim 1 which includes incubating at a temperature of about 90° C. for about 3 minutes.

8. A method for the detection of penicillinase in a body fluid sample which method comprises:
   (a) contacting a body fluid sample selected from the group consisting of cerebrospinal fluid, pleural fluid, peritoneal fluid, urine and blood to be detected for penicillinase with an activated charcoal absorbent particulate to absorb any interfering penicillin and recovering an essentially charcoal-free, penicillin-free supernatant;
   (b) incubating said supernatant with cells of a *Bacillus stearothermophilus* microorganism and a labeled $C^{14}$ penicillin beta-lactam capable of binding to the microorganism cells under such conditions to permit any penicillinase present to enzymatically degrade the $C^{14}$ penicillin and permit the remaining intact $C^{14}$ penicillin and permit the remaining intact $C^{14}$ penicillin to bind to the cells of the microorganism;
   (c) removing the microorganism cells from the microorganism supernatant mixture;
   (d) determining the amount of bound labeled $C^{14}$ penicillin with the removed microorganism cells; and
   (e) comparing the amount of bound labeled $C^{14}$ penicillin with a control sample to obtain a determination of the amount of penicillinase present in the body fluid sample.

* * * * *